United States Patent
Cook

(10) Patent No.: US 10,085,820 B2
(45) Date of Patent: Oct. 2, 2018

(54) DISPOSABLE DENTAL DAM

(71) Applicant: Carl E Cook, Cortland, OH (US)

(72) Inventor: Carl E Cook, Cortland, OH (US)

(*) Notice: Subject to any disclaimer, the term of this patent is extended or adjusted under 35 U.S.C. 154(b) by 0 days.

(21) Appl. No.: 15/122,343

(22) PCT Filed: Mar. 3, 2015

(86) PCT No.: PCT/US2015/018488
§ 371 (c)(1),
(2) Date: Aug. 29, 2016

(87) PCT Pub. No.: WO2015/134498
PCT Pub. Date: Sep. 11, 2015

(65) Prior Publication Data
US 2016/0367338 A1 Dec. 22, 2016

Related U.S. Application Data

(60) Provisional application No. 61/947,650, filed on Mar. 4, 2014.

(51) Int. Cl.
*A61C 9/00* (2006.01)
*A61C 5/12* (2006.01)
(Continued)

(52) U.S. Cl.
CPC ............ *A61C 5/122* (2013.01); *A61C 5/82* (2017.02); *A61C 9/0006* (2013.01); *A61C 13/34* (2013.01); *A61C 2202/00* (2013.01)

(58) Field of Classification Search
CPC ......... A61C 5/122; A61C 5/82; A61C 9/0006; A61C 13/34; A61C 2202/00; A61C 9/00
(Continued)

(56) References Cited

U.S. PATENT DOCUMENTS 3,360,860 A * 1/1968 Roland ................ A61C 9/0006
264/16
3,443,720 A * 5/1969 Al-Roy ................ B65D 43/021
220/791
(Continued)

FOREIGN PATENT DOCUMENTS

| WO | 8806869 | 9/1988 |
|----|---------|--------|
| WO | 8806869 A | 9/1988 |
| WO | 2015134498 | 9/2015 |

OTHER PUBLICATIONS

International Search Report and Written Opinion from corresponding International Application No. PCT/US2015/018488, dated May 18, 2015.
(Continued)

*Primary Examiner* — Heidi M Eide
*Assistant Examiner* — Mirayda A Aponte
(74) *Attorney, Agent, or Firm* — Tucker Ellis LLP

(57) ABSTRACT

A dental dam apparatus is provided for use with an associated dental molding system including an impression tray and a pour dam. The dental dam includes a substantially planar body member, and an attachment portion on the front edge of the body member. The body member defines a generally "U" shaped front edge and a generally straight rear edge extending between ends of the "U" shaped front edge. The attachment portion is configured to selectively engage a generally "U" shaped inner surface of the impression tray and to attach the body member with the tray. In that way, dental molding material poured into the dental molding system with the pour dam surrounding the impression tray and with the body member attached with the impression tray is blocked by the body member from entering into a portion of an area defined by the "U" shaped inner surface of the impression tray.

18 Claims, 5 Drawing Sheets

(51) Int. Cl.
*A61C 13/34* (2006.01)
*A61C 5/82* (2017.01)

(58) Field of Classification Search
USPC .......................... 433/45, 229; 264/16; 435/2
See application file for complete search history.

(56) References Cited

U.S. PATENT DOCUMENTS

| | | |
|---|---|---|
| 6,318,997 B1 | 11/2001 | Mayweather |
| 2004/0096800 A1* | 5/2004 | Tucker ................. A61C 9/0006 433/38 |
| 2011/0129791 A1* | 6/2011 | Rabinowitz .............. A61C 9/00 433/37 |

OTHER PUBLICATIONS

International Preliminary Report on Patentability from corresponding International Application No. PCT/US2015/018488, dated May 18, 2015.

* cited by examiner

DISPOSABLE DENTAL DAM

CROSS-REFERENCE TO RELATED APPLICATIONS

This application is a national phase of International Application No. PCT/US2015/018488 filed Mar. 3, 2015 and published in the English language.

This application claims the benefit of U.S. Provisional Application No. 61/947,650, filed Mar. 4, 2014.

BACKGROUND

In the traditional "pour up" of dental plaster being poured or otherwise inserted into a mold cavity defined by a bottom impression tray and sidewalls defined by a thin metal or wax footer, wetted crumbled paper or other materials are often used to prevent the dental plaster from undesirably entering onto areas of the mold cavity. For example, dental plaster often enters into the area between the wings of full arch impression trays. This is wasteful of the material and also requires extra time and effort in the molding process to remove the unwanted molding material from these areas.

Although the wetted crumbled paper or other materials are somewhat useful in helping to prevent the dental plaster from entering onto undesired areas of the mold cavity, this technique is messy, unscientific, and prone to substandard results.

SUMMARY

The following presents a simplified overview of the example embodiments in order to provide a basic understanding of some aspects of the example embodiments. This overview is not an extensive overview of the example embodiments. It is intended to neither identify key or critical elements of the example embodiments nor delineate the scope of the appended claims. Its sole purpose is to present some concepts of the example embodiments in a simplified form as a prelude to the more detailed description that is presented later.

In an embodiment described herein, a dental dam apparatus is provided for use with an associated dental molding system including an impression tray and a pour dam configured to selectively surround the impression tray during a dental molding process. The dental dam apparatus has a generally "U" shaped front edge and an attachment portion on the front edge, wherein the attachment portion is configured to selectively engage a generally "U" shaped inner surface of the associated impression tray for attaching the body member of the dental dam apparatus with the associated impression tray. In this way, with the associated pour dam tightly surrounding the impression tray and with the body member of the dental dam apparatus suitably attached to the impression tray, dental molding material poured into the dental molding system is blocked by the body member from entering into a portion of an area defined by the "U" shaped inner surface and a height of the associated impression tray.

In accordance with a further embodiment described herein, a dental molding system is provided comprising an impression tray, a pour dam configured to selectively surround the impression tray during a dental molding process, and a dental dam apparatus. The dental dam apparatus has a generally "U" shaped front edge and an attachment portion on the front edge, wherein the attachment portion is configured to selectively engage a generally "U" shaped inner surface of the associated impression tray for attaching the body member with the associated impression tray. In this way, with the associated pour dam surrounding the impression tray and with the body member attached to the impression tray, dental molding material poured into the dental molding system is blocked by the body member from entering into a portion of an area defined by the "U" shaped inner surface and a height of the associated impression tray.

DRAWINGS

The accompanying drawings incorporated herein and forming a part of the specification illustrate the example embodiments.

FIG. 3 is a top plan view of a disposable dental dam apparatus formed in accordance with an example embodiment;

DETAILED DESCRIPTION

Figure 1:
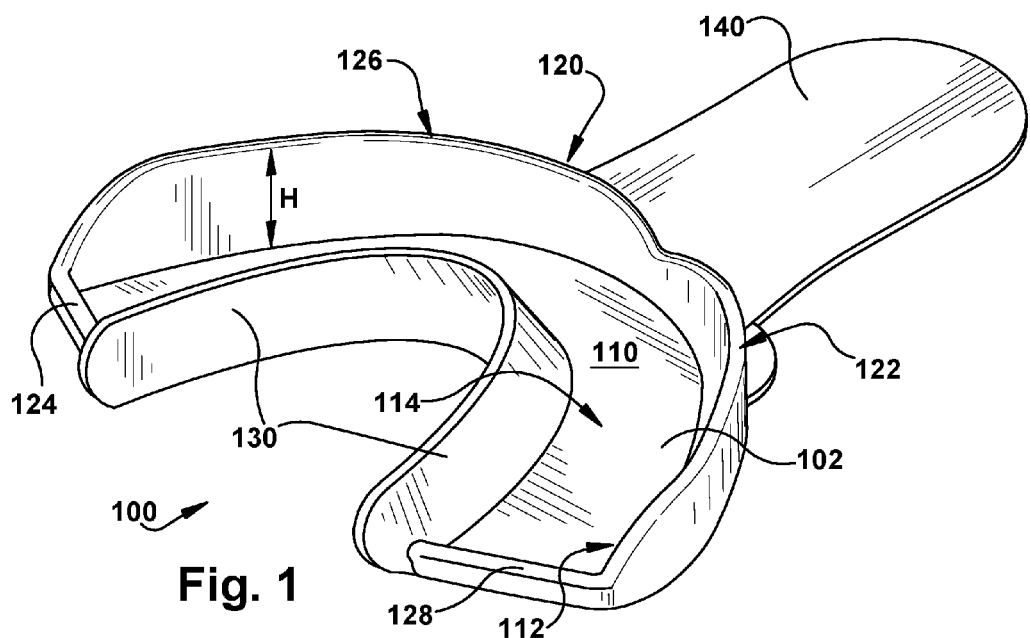
FIG. 1 is a perspective view of an impression tray in accordance with an example embodiment.

With reference now to the drawings wherein the showings are for purposes of describing the example embodiments and not limiting same, FIG. 1 is a perspective view of an impression tray 100 formed in accordance with an example embodiment. Although the illustrated impression tray 100 is of the "full arch" variety, it is to be appreciated that the embodiments herein and described below are equally suitable for use with and in combination with any size or type of dental molding trays. The impression tray 100 has an overall general "U" shape as shown for purposes of adapting the impression tray 100 for use in making in situ impressions of the upper or lower rows of teeth carried in the mouths of human or animal patients.

The impression tray 100 shown in the Figure is a full arch lower impression tray 102 for making an in situ impression of the lower row of teeth. However, it is to be understood and appreciated that the embodiments herein are not limited to upper or lower impression trays or of impressions trays for human or animal patients, but the embodiments are for use with molding any one or more structures wherein a disposable dam apparatus may find use in blocking molding material from entering into any selected one or more region(s) and/or area(s) during the "pour up" or during any other step in a molding process.

The illustrated impression tray 100 has a lower "U" shaped bottom floor 110 surrounded by a continuous upstanding outer wall 112. The wall 112 is disposed in a generally perpendicular arrangement relative to the floor 110 and has a substantially uniform height H. The floor 110 and wall 112 define a generally "U" shaped volume 114 provided to receive and hold impression putty 200 (shown in FIG. 2). For convenience during use, a front portion 120 of the wall 112 carries a forwardly directed handle member 140 configured for grasping by hand, such as between the thumb and index finger, by a dental assistant or the like for assisting with the ease and accuracy of inserting the impression tray 100 into the mouth of a patient and, therefore, for locating and suitably positioning the tray carrying the putty onto the target one or more teeth.

The outer wall 112 of the impression tray 100 further includes a right forward wall portion 122, a right rearward wall portion 128, a left forward wall portion 126, and a left rearward wall portion 124. Lastly, the outer wall 112 includes a generally "U" shaped posterior wall portion 130 disposed between and connecting the right rearward wall portion 128 with the left rearward wall portion 124. The right forward wall portion 122, the right rearward wall portion 128, the left forward wall portion 126, the left rearward wall portion 124, and the posterior wall portion 130 are mutually coupled together or are otherwise integrally formed together thereby defining the outer wall 112 as shown and described.

The posterior wall portion 130 is selectively positioned during use of the tray in the patient's mouth between the patient's tongue (not shown) and the patient's teeth (not shown), wherein the patient's teeth are received into putty 200 (FIG. 2) that is pre-disposed in the volume 114. The posterior wall portion 130 of the outer wall 112 preferably has a structure and/or a finish suitably configured for attachment with a portion of a disposable dental dam 300 (FIG. 3) in accordance with an embodiment to be described in greater detail below.

Figure 2:
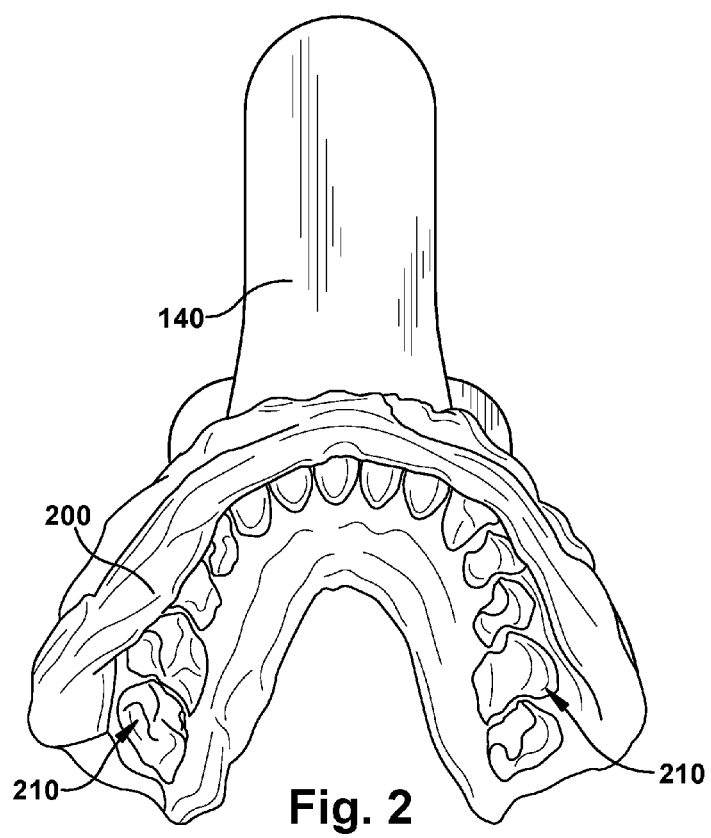
FIG. 2 is a top plan view of the impression tray of FIG. 1 showing molding material and a negative dental impression formed in the molding material.
Figure 3A:
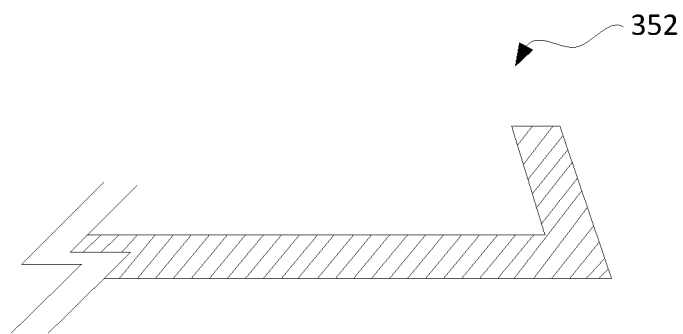
FIG. 3a is a cross-sectional view of a disposable dental dam apparatus formed in accordance with an example embodiment illustrating a folded front edge.
Figure 3B:
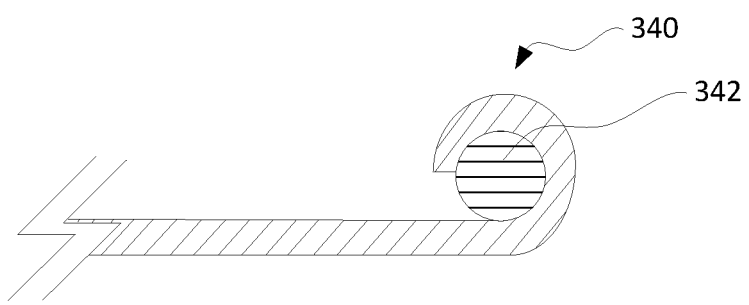
FIG. 3b is a cross-sectional view of a disposable dental dam apparatus formed in accordance with an example embodiment illustrating a flexible wire embedded in a rolled front edge.

FIG. 2 is a top plan view of the impression tray 100 of FIG. 1 showing impression putty 200 with "negative" impressions 210 of the patient's teeth formed therein. During use, the impression putty 200 is first supplied into the volume 114 defined by the outer wall 112 surrounding the bottom floor 110 of the impression tray 100. Thereafter, the collective setup of the tray 100 carrying the putty 200 is inserted into the patient's mouth whereby the negative impressions 210 of the patient's teeth may be made by the patient biting down on the setup wherein the teeth enter into the putty and leave an impression thereof in the putty after the teeth and putty are separated following a short curing period, which negative impression remains set in the putty after removal of the setup from the patient's mouth.

Figure 4:
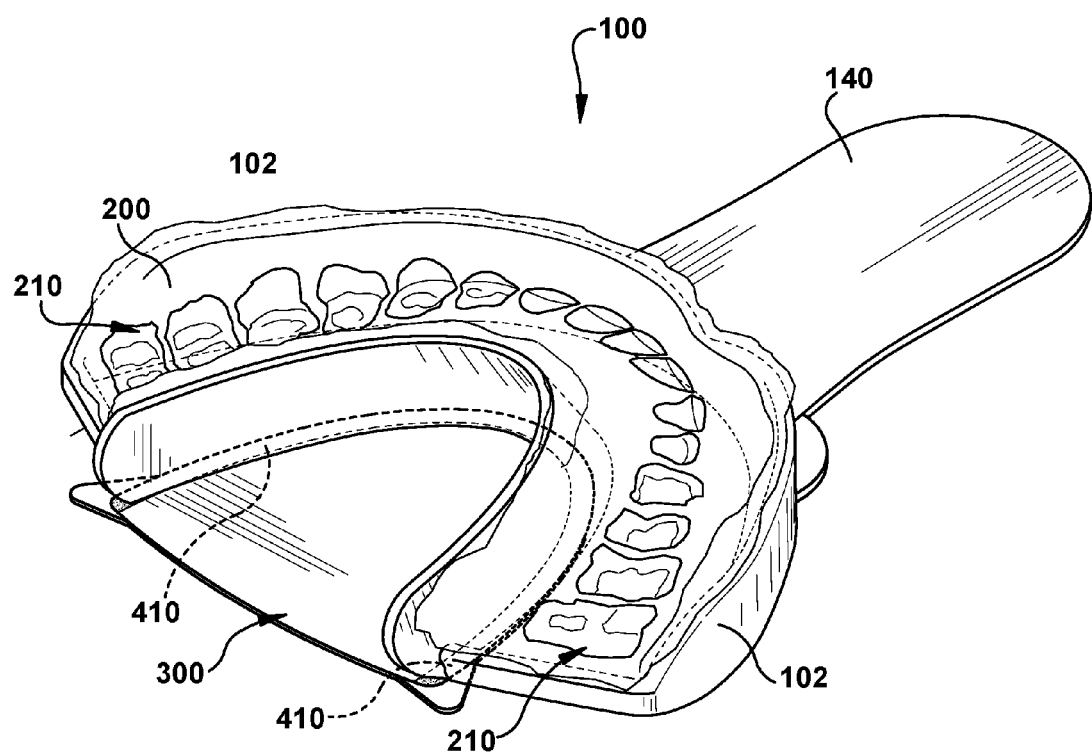
FIG. 4 is a perspective view showing the disposable dental dam of FIG. 3 attached with the impression tray with the molding material of FIG. 2.

FIG. 3 is a top plan view of a disposable dental dam apparatus 300 formed in accordance with an example embodiment, and FIG. 4 is a perspective view showing the dental dam apparatus 300 of FIG. 3 attached with the molding tray 100 of FIG. 2 carrying the impression putty 200 with the negative impression 210 of the patient's teeth defined therein. In the example shown the dental dam apparatus 300 includes a substantially planar body member 310 and an attachment portion 350. The substantially planar body member 310 defines a generally "U" shaped front edge 320 and a generally straight rear edge 330 extending between ends 321, 322 of the generally "U" shaped front edge 320. The attachment portion 350 is disposed on the front edge 320 of the substantially planar body member 310, and is configured to selectively engage a generally "U" shaped inner surface of the "U" shaped posterior wall portion 130 (FIG. 1) of the associated impression tray 100 to attach the body member 310 of the dental dam apparatus 300 with the associated impression tray 100.

In the example embodiment, the attachment portion 350 disposed on the front edge 320 of the body member 310 is configured to attach with the posterior wall portion 130 of the outer wall 112 of the impression tray 100. In this way and with reference to FIGS. 5 and 6, dental molding material 610 that is poured into a dental molding system 500 with an associated pour dam 510 surrounding the impression tray 100 and with the body member 310 of the dental dam 300 attached with the impression tray 102 is blocked by the body member 310 of the dental dam 300 from entering into a portion of an area defined by the posterior wall portion 130 and a height H of the impression tray 100.

In one example embodiment, the substantially planar body member 310 of the dental dam apparatus 300 is formed of a mesh material. For example, mesh materials may include, for example, nylon, plastic or other woven one or more material(s) of varying compositional makeup having desirable properties such as high resiliency, flexibility, strength, and low cost. In another example embodiment, the substantially planar body member 310 of the dental dam apparatus 300 is formed of a semi-flexible rubber material. Suitable rubber materials may include, for example, latex, blended latex/rubber, or other one or more material(s) of varying compositional makeup having desirable properties such as high resiliency, flexibility, strength, and low cost. In a further example embodiment, the substantially planar body member 310 of the dental dam apparatus 300 is formed of a paper material. In yet a still further example embodiment, the substantially planar body member 310 of the dental dam apparatus is 300 is formed of a plastic material. In a further example embodiment, the substantially planar body member 310 of the dental dam apparatus 300 is formed of a waxed paper material.

Forming the dental dam apparatus from a flexible material such as rubber or a latex material is advantageous for use of a single size dam apparatus with a range of sizes of impression trays wherein the flexible dam apparatus may be sized in a relaxed state to directly attach with a child-sized impression tray, yet be stretched to attach with a large adult sized impression tray in accordance with the underlying material forming the dental dam apparatus.

In the example embodiment, the attachment portion 350 of the dental dam apparatus 300 comprises an adhesive material 360 disposed on the generally "U" shaped front edge 320 of the body member 310. The adhesive material 360 is preferably disposed uninterrupted along the generally "U" shaped front edge 320 of the body member 310 thereby forming, when attached with the wall portion 130 of the impression tray 100, a continuous seal 410 (FIG. 4) between the body member 310 and the generally posterior wall portion 130 of the impression tray 100.

In an example embodiment, the attachment portion 350 comprises a folded front edge 352 (FIG. 3a) of the body member 310 and an adhesive material 360 disposed on the folded front edge 352 of the body member 310. The adhesive material 360 disposed uninterrupted along the folded front edge 352 of the body member 310 thereby forms a continuous seal 410 between the body member 310 and the generally posterior wall portion 130 of the impression tray 100.

In a further example embodiment, the attachment portion 350 comprises a rolled front edge 340 (FIG. 3b) of the body member 310, a resilient flexible wire 342 embedded within the rolled front edge of the body member, and an adhesive material 360 disposed on the rolled front edge of the body member 310. The embedded resilient flexible wire helps to stabilize the desired fit of the dental dam apparatus to the impression tray, and the adhesive material 360 disposed uninterrupted along the rolled front edge 352 of the body member 310 thereby forms a continuous seal 410 (FIG. 4) between the body member 310 and the generally posterior wall portion of the impression tray 100.

In still yet a further example embodiment, the attachment portion 350 comprises an extension portion (not shown) of the body member 310 wherein the extension portion is configured to be received into, and the wall portion 130 of the impression tray 100 is configured to receive, the extension portion when the dental dam apparatus 300 is inserted into the region between the wings of the tray. A continuous groove along the wall portion 130 (not shown) of the impression tray suitably receives the extension portion of the dental dam thereby holding the dental dam apparatus 300 and the impression tray 100 in a relative fixed or locked position.

In addition to the above, in accordance with a still further example embodiment and with reference once again to FIG. 3, the dental dam apparatus 300 includes a set of one or more tab members 302 disposed on the body member 310 adjacent the ends 321, 322 of the generally "U" shaped front edge 320. In this example embodiment, the set of one or more tab members 302 comprises a set of two (2) tab members 304, 306 having a generally triangular conformation and being disposed on the body member 310 adjacent the ends 321, 322 of the generally "U" shaped front edge 320.

During use of the dental dam apparatus of the example embodiment described including the tab members 302, the tab members 304, 306 are configured to selectively engage the generally posterior wall portion 130 of the impression tray 100 for blocking additional dental molding material poured into the dental molding system 500 (FIG. 5) from entering into an area of the associated dental molding system beyond the straight rear edge 330 of the body member 310 opposite from the area defined by the posterior wall portion 130 and the height H of the associated impression tray.

Figure 5:
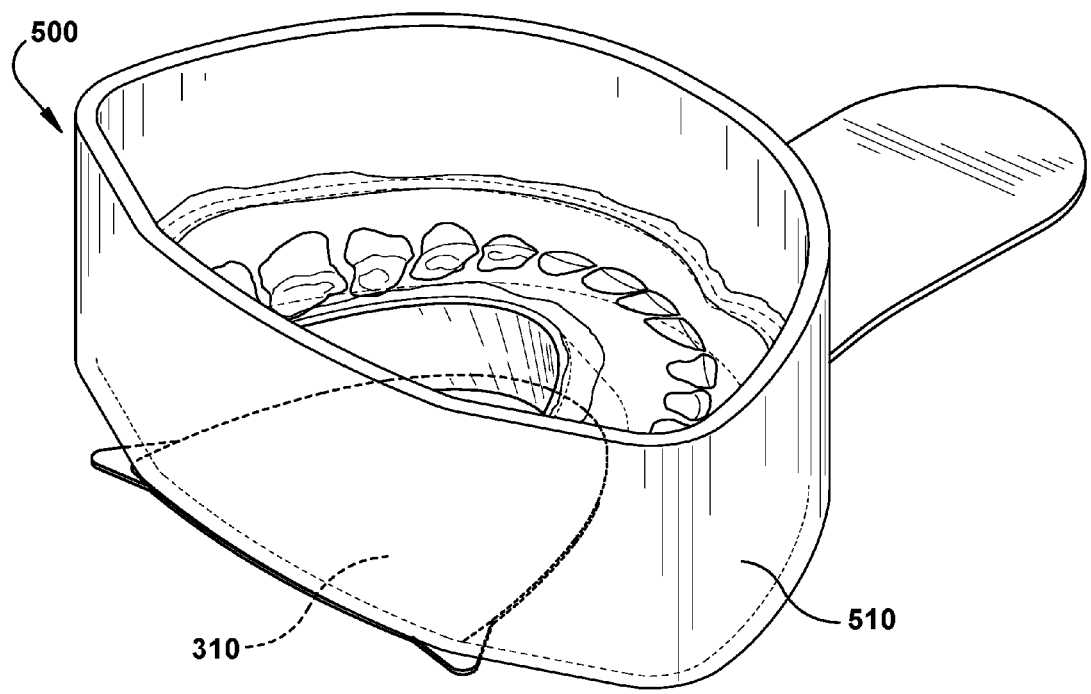
FIG. 5 is a perspective view of a dental molding system in accordance with an example embodiment showing the impression tray of FIGS. 1 and 2, the dental dam apparatus of FIG. 3 attached with the impression tray as in FIG. 4, and including a pour dam configured to selectively surround the impression tray during a dental molding process.
Figure 6:
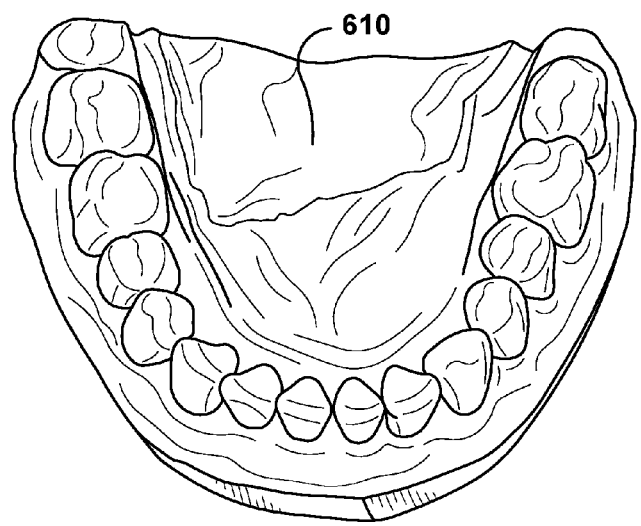
FIG. 6 is a top plan view of a dental model resulting after applying suitable molding material to the dental molding system of FIG. 5.

In a further example embodiment and as shown in FIG. 5, a dental molding system 500 includes an impression tray 100, and a dental dam apparatus 300 affixed to the impression tray. In this embodiment, the dental dam apparatus 300 comprises a substantially planar body member defining a generally "U" shaped front edge and a generally straight rear edge extending between ends of the generally "U" shaped front edge, and an attachment portion on the front edge of the substantially planar body member, wherein the attachment portion is configured to selectively engage a generally "U" shaped inner surface of the impression tray and to attach the body member with the impression tray. In this way, dental molding material poured into the dental molding system with the body member attached with the impression tray is blocked by the body member from entering into a portion of an area defined by the "U" shaped inner surface and a height of the impression tray.

In yet a still further example embodiment and as also shown in FIG. 5, a dental molding system 500 includes an impression tray 100, 102, a pour dam 510 configured to selectively surround the impression tray 100, 102 during a dental molding process, and a dental dam apparatus 300. A rubber band (not shown) or similar device may be used as necessary or desired to secure the pour dam 510 with the impression tray 100 to prevent relative movement therebetween. In this embodiment, the dental dam apparatus 300 comprises a substantially planar body member defining a generally "U" shaped front edge and a generally straight rear edge extending between ends of the generally "U" shaped front edge, and an attachment portion on the front edge of the substantially planar body member, wherein the attachment portion is configured to selectively engage a generally "U" shaped inner surface of the impression tray and to attach the body member with the impression tray. In this way, dental molding material poured into the dental molding system with the body member attached with the impression tray is blocked by the body member from entering into a portion of an area defined by the "U" shaped inner surface and a height of the impression tray.

Figure 7:
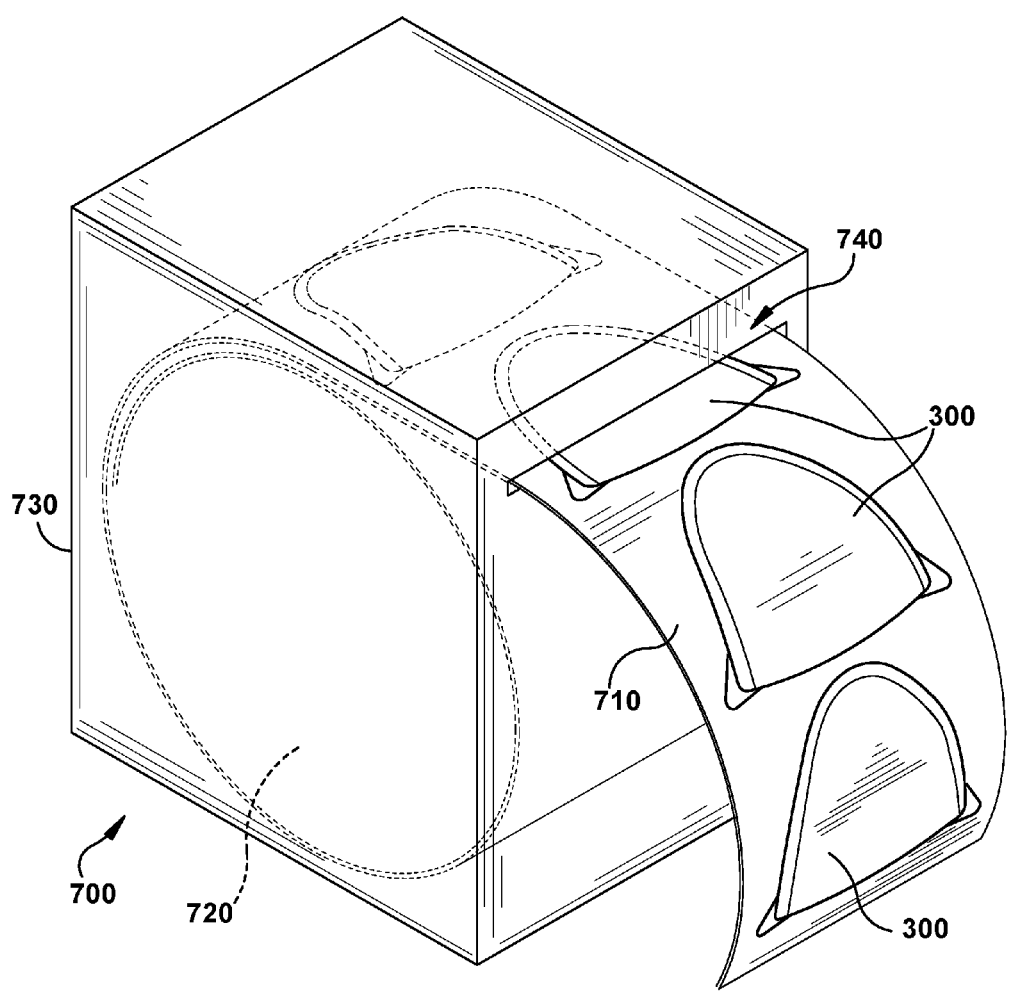
FIG. 7 is an illustration showing a plurality if the disposable dental dam apparatus of FIG. 3 carried on a convenient roll for dispensing the dental dam apparatus as needed during a dental molding process.

FIG. 7 is an illustration showing a dental dam dispensing system 700 in accordance with a further example embodiment. With reference now to that Figure, a plurality of the disposable dental dam apparatus 300 of FIG. 3 are carried on a dispensing strip 710 coiled on one end into a convenient roll 720 disposed in a dispensing box 730 for dispensing the dental dam apparatus 300 as needed by removing the dam apparatus from the free end 740 of the dispensing strip 710 extending from an opening 740 provided in the box.

In other embodiments, one or more dental dam apparatus are attached to a small waxed paper dispenser affixed to a stiffer, cardboard backing.

Described above are example embodiments. It is, of course, not possible to describe every conceivable combination of components or methodologies, but one of ordinary skill in the art will recognize that many further combinations and permutations of the example embodiments are possible. Accordingly, this application is intended to embrace all such alterations, modifications and variations that fall within the spirit and scope of the appended claims interpreted in accordance with the breadth to which they are fairly, legally and equitably entitled.

Having thus described example embodiments, it is now claimed:

1. A dental dam apparatus for use with an associated dental molding system including an impression tray and a pour dam configured to selectively surround the impression tray and confine associated dental molding material to within the pour dam during a dental molding process, the dental dam apparatus comprising:

a flexible body member defining a generally "U" shaped front edge and a generally straight rear edge extending between ends of the generally "U" shaped front edge; and an adhesive attachment portion on the front edge of the flexible body member, the adhesive attachment portion being configured to selectively engage a generally "U" shaped inner surface of the associated impression tray and to selectively attach the flexible body member with the associated impression tray by holding the flexible body member onto the generally "U" shaped inner surface of the associated impression tray, wherein the adhesive attachment portion comprises: i) a folded front edge of the flexible body member, and ii) an adhesive material disposed on the folded front edge of the flexible body member, whereby the associated dental molding material poured into the dental molding system with the associated pour dam surrounding the associated impression tray and with the flexible body member attached with the associated impression tray is blocked by the flexible body member from entering into a portion of an area defined by the "U" shaped inner surface and a height of the associated impression tray.

2. The dental dam apparatus according to claim 1, wherein:
the adhesive material is disposed uninterrupted along the folded front edge of the flexible body member, the adhesive material forming a continuous seal between the flexible body member and the generally "U" shaped inner surface of the associated impression tray.

3. The dental dam apparatus according to claim 1, further comprising:
a set of one or more tab members disposed on the flexible body member adjacent the ends of the generally "U" shaped front edge.

4. The dental dam apparatus according to claim 3, wherein:
the set of one or more tab members comprises a set of two (2) tab members having a generally triangular conformation and being disposed on the flexible body member adjacent the ends of the generally "U" shaped front edge.

5. The dental dam apparatus according to claim 4, wherein:
the set of two tab members are configured to selectively engage the generally "U" shaped inner surface of the associated impression tray for blocking additional dental molding material poured into the dental molding system from entering into an area of the associated dental molding system beyond the straight edge of the flexible body member opposite from the area the defined by the "U" shaped inner surface and the height of the associated impression tray.

6. A dental dam apparatus for use with an associated dental molding system including an impression tray and a pour dam configured to selectively surround the impression tray and confine associated dental molding material to within the pour dam during a dental molding process, the dental dam apparatus comprising:
a flexible body member defining a generally "U" shaped front edge and a generally straight rear edge extending between ends of the generally "U" shaped front edge; and
an adhesive attachment portion on the front edge of the flexible body member, the adhesive attachment portion being configured to selectively engage a generally "U" shaped inner surface of the associated impression tray and to selectively attach the flexible body member with the associated impression tray by holding the flexible body member onto the generally "U" shaped inner surface of the associated impression tray, wherein the adhesive attachment portion comprises: i) a rolled front edge of the flexible body member, and ii) an adhesive material disposed on the rolled front edge of the flexible body member,
whereby the associated dental molding material poured into the dental molding system with the associated pour dam surrounding the associated impression tray and with the flexible body member attached by the flexible body member from entering into a portion of an area defined by the "U" shaped inner surface and a height of the associated impression tray.

7. The dental dam apparatus according to claim 6, wherein:
wherein the adhesive material is disposed uninterrupted along the generally "U" shaped front edge of the flexible body member, the adhesive material forming a continuous seal between the flexible body member and the generally "U" shaped inner surface of the associated impression tray.

8. The dental dam apparatus according to claim 6, further comprising:
a resilient flexible wire member disposed within the rolled front edge of the flexible body member for stabilizing the front edge relative to the associated impression tray, wherein the adhesive material is disposed uninterrupted along the rolled front edge of the flexible body member, the adhesive material forming a continuous seal between the flexible body member and the generally "U" shaped inner surface of the associated impression tray.

9. A dental molding system comprising:
an impression tray;
a pour dam configured to selectively surround the impression tray and confine associated dental molding material during a dental molding process to within an area defined by the pour dam; and
a dental dam apparatus comprising:
a flexible body member defining a generally "U" shaped front edge and a generally straight rear edge extending between ends of the generally "U" shaped front edge; and
an adhesive attachment portion on the front edge of the flexible body member, the adhesive attachment portion being configured to selectively engage a generally "U" shaped inner surface of the impression tray and to selectively attach the flexible body member with the impression tray by holding the flexible body member onto the generally "U" shaped inner surface of the associated impression tray, wherein the adhesive attachment portion comprises: i) a folded front edge of the flexible body member, and ii) an adhesive material disposed on the folded front edge of the flexible body member,
whereby the associated dental molding material poured into the dental molding system with the pour dam surrounding the impression tray and with the flexible body member attached with the impression tray is blocked by the flexible body member from entering into a portion of an area defined by the "U" shaped inner surface and a height of the impression tray.

10. The dental molding system according to claim 9, wherein:
the adhesive material is disposed uninterrupted along the folded front edge of the flexible body member, the adhesive material forming a continuous seal between the flexible body member and the generally "U" shaped inner surface of the associated impression tray.

11. The dental molding system according to claim 9, further comprising:
a set of one or more tab members disposed on the flexible body member adjacent the ends of the generally "U" shaped front edge.

12. The dental molding system according to claim 11, wherein:
the set of one or more tab members comprises a set of two (2) tab members having a generally triangular conformation and being disposed on the flexible body member adjacent the ends of the generally "U" shaped front edge.

13. The dental molding system according to claim 12, wherein:
the set of two tab members are configured to selectively engage the generally "U" shaped inner surface of the associated impression tray for blocking additional dental molding material poured into the dental molding system from entering into an area of the associated dental molding system beyond the straight edge of the flexible body member opposite from the area the defined by the "U" shaped inner surface and the height of the associated impression tray.

14. A dental molding system comprising:
an impression tray;
a pour dam configured to selectively surround the impression tray and confine associated dental molding material during a dental molding process to within an area defined by the pour dam; and
a dental dam apparatus comprising:
a flexible body member defining a generally "U" shaped front edge and a generally straight rear edge extending between ends of the generally "U" shaped front edge; and
an adhesive attachment portion on the front edge of the flexible body member, the adhesive attachment portion being configured to selectively engage a generally "U" shaped inner surface of the impression tray and to selectively attach the flexible body member with the impression tray by holding the flexible body member onto the generally "U" shaped inner surface of the associated impression tray,
wherein the adhesive attachment portion comprises: i) a rolled front edge of the flexible body member, and ii) an adhesive material disposed on the rolled front edge of the flexible body member,
whereby the associated dental molding material poured into the dental molding system with the pour dam surrounding the impression tray and with the flexible body member attached with the impression tray is blocked by the flexible body member from entering into a portion of an area defined by the "U" shaped inner surface and a height of the impression tray.

15. The dental molding system according to claim 14, wherein:
wherein the adhesive material is disposed uninterrupted along the generally "U" shaped front edge of the flexible body member, the adhesive material forming a continuous seal between the flexible body member and the generally "U" shaped inner surface of the associated impression tray.

16. The dental molding system according to claim 14, further comprising:

a resilient flexible wire member disposed within the rolled front edge of the flexible body member for stabilizing the front edge relative to the associated impression tray, wherein the adhesive material is disposed uninterrupted along the rolled front edge of the flexible body member thereby forming a continuous seal between the flexible body member and the generally "U" shaped inner surface of the associated impression tray.

17. A dental dam apparatus for use with an associated dental molding system including an impression tray and a pour dam configured to selectively surround the impression tray and confine associated dental molding material to within the pour dam during a dental molding process, the dental dam apparatus comprising:
a flexible body member defining a generally "U" shaped front edge and a generally straight rear edge extending between ends of the generally "U" shaped front edge, the flexible body member being stretchable from an un-stretched relaxed state to an unrelaxed stretched state for use with associated impression trays of the associated dental molding system having a range of sizes from a first size to a second size larger than the first size; and
an adhesive attachment portion on the front edge of the flexible body member, wherein the adhesive attachment portion comprises: i) a folded or rolled front edge of the flexible body member, and ii) an adhesive material disposed on the folded or rolled front edge of the flexible body member, the adhesive attachment portion being configured to:
selectively engage a generally "U" shaped inner surface of a first associated impression tray having the first size and to selectively attach the flexible body member with the first associated impression tray by holding the flexible body member in the un-stretched relaxed state onto the generally "U" shaped inner surface of the first associated impression tray, and
selectively engage a generally "U" shaped inner surface of a second associated impression tray having the second size and to selectively attach the flexible body member with the second associated impression tray by holding the flexible body member in the un-relaxed stretched state onto the generally "U" shaped inner surface of the second associated impression tray.

18. The dental dam apparatus according to claim 17, wherein:
the adhesive attachment portion comprises an adhesive material disposed uninterrupted along the generally "U" shaped front edge of the flexible body member, the adhesive material forming a continuous seal between the flexible body member and the generally "U" shaped inner surfaces of the first or second associated impression trays.

* * * * *